United States Patent [19]
Petzoldt et al.

[11] 4,416,985
[45] Nov. 22, 1983

[54] PROCESS FOR PREPARING 3β,7β-DIHYDROXY-Δ⁵-STEROIDS

[75] Inventors: Karl Petzoldt; Rudolf Wiechert; Henry Laurent; Klaus Nickisch; Dieter Bittler, all of Berlin, Fed. Rep. of Germany

[73] Assignee: Schering, Aktiengesellschaft, Berlin and Bergkamen, Fed. Rep. of Germany

[21] Appl. No.: 317,822

[22] Filed: Nov. 3, 1981

[30] Foreign Application Priority Data

Nov. 3, 1980 [DE] Fed. Rep. of Germany ....... 3042136

[51] Int. Cl.³ .......................... C12P 33/06; C07J 7/00
[52] U.S. Cl. .................................... 435/58; 260/397.4
[58] Field of Search .......................................... 435/58

[56] References Cited
U.S. PATENT DOCUMENTS 4,336,332 6/1982 Fujiwara et al. ...................... 435/58

Primary Examiner—Alvin E. Tanenholtz
Attorney, Agent, or Firm—Millen & White

[57] ABSTRACT

A process for preparing a 3β,7β-dihydroxy-Δ⁵steroid of the formula

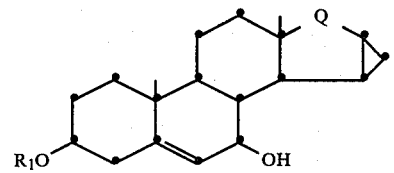

wherein
Q is

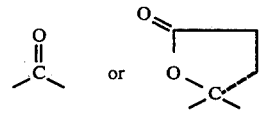

and
$R_1$ is hydrogen, trimethylacetyl, tert-butyldimethylsilyl, dimethyl-2-(3-methylbutyl)silyl or tribenzylsilyl,
comprises fermenting a 3β-hydroxy-Δ⁵-steroid of the formula

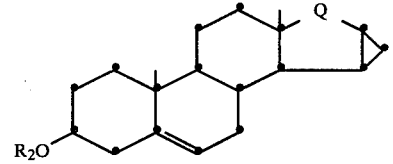

wherein
Q is as defined above, and
$R_2$ is hydrogen or alkanoyl of 2–6 carbon atoms,
with a culture of *Botryodiplodia malorum* to obtain the corresponding 3β,7β-dihydroxy-Δ⁵-steroid; and, optionally, reacting the resultant product with trimethylacetic anhydride, tert-butyldimethylsilyl chloride, dimethyl-2-(3-methylbutyl)silyl chloride, or tribenzylsilyl chloride.

5 Claims, No Drawings

PROCESS FOR PREPARING 3β,7β-DIHYDROXY-Δ⁵-STEROIDS

BACKGROUND OF THE INVENTION

The present invention relates to a process for preparing 3β,7β-dihydroxy-Δ⁵-steroids.

SUMMARY OF THE INVENTION

It is an object of this invention to provide an improved process for preparing 3β,7β-dihydroxy-Δ⁵-steroids.

Upon further study of specification and appended claims, further objects and advantages of this invention will become apparent to those skilled in the art.

These objects have been achieved by providing a process for preparing a 3β,7β-dihydroxy-Δ⁵-steroid of Formula I

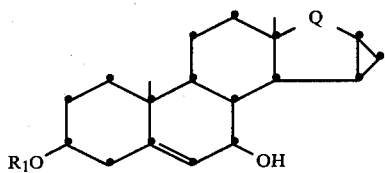

wherein
Q is

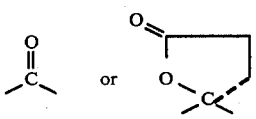

and
$R_1$ is hydrogen, trimethylacetyl, tert-butyldimethylsilyl, dimethyl-2-(3-methylbutyl)silyl or tribenzylsilyl,
comprising fermenting a 3β-hydroxy-Δ⁵-steroid of Formula II

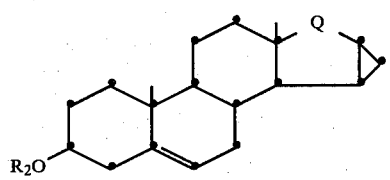

wherein
Q is as defined above, and
$R_2$ is hydrogen or alkanoyl of 2-6 carbon atoms,
with a culture of *Botryodiplodia malorum* to obtain the corresponding, 3β,7β-dihydroxy-Δ⁵-steroid; and, optionally, reacting the resultant product with trimethylacetic anhydride, tert-butyldimethylsilyl chloride, dimethyl-2-(3-methylbutyl)silyl chloride, or tribenzylsilyl chloride.

DETAILED DISCUSSION

3β,7β-dihydroxy-Δ⁵-steroids of Formula I are important intermediates in part of conventional syntheses of pharmacologically active steroids, such as the aldosterone-antagonist, 6β,7β;15β,16β-dimethylene-3-oxo-17α-pregn-4-ene-21,17-carbolactone, as demonstrated in the Examples herein.

Using the process of this invention, it is possible to produce the product compounds in high yield from the corresponding compounds unsubstituted in the 7-position.

The first reaction of the process of this invention is conducted under conventional conditions usually employed in microbiological hydroxylations of steroids with fungal cultures. Details can be determined by fully conventional considerations and are in accordance with A Capec et al., *Microbial Transformation of Steroids*, Academic Press, Prague, 1966, especially pages 65-68, whose disclosure is incorporated by reference herein.

Thus, using the customary preliminary tests, the most favorable fermentation conditions can first be determined. For example, selection can thusly be made of the most advantageous nutrient medium, the suitable substrate solvent or suspension agent, the substrate concentration, the technical conditions, e.g., temperature, aeration, pH value, and the optimum periods for germination, addition of substrate, and substrate contact on the enzyme of the microorganism. Such selections can be made by conventional analyses, especially by thin-layer chromatography.

It has been determined, for example, in this connection, that it is suitable to use concentrations of about 100-2,000 mg of substrate per liter of nutrient medium. The pH is preferably set at a value in the range of 5 to 7. The incubation temperature ranges from 20° to 40° C., preferably from 25° to 35° C. For aeration, 0.5-5 liters of air per minute per liter of culture broth is preferably introduced. The conversion of the substrate is advantageously controlled by analysis of sample extracts using thin-layer chromatography. The fermentation period is usually about 20-80 hours.

After fermentation has taken place, the fermentation products can be isolated conventionally. The isolation can be accomplished, for example, by extracting the fermentation batches with an organic solvent immiscible with water, such as ethyl acetate, butyl acetate, or methyl isobutyl ketone; concentrating the extracts; and, optionally, purifying the resultant crude products by chromatography and/or crystallization.

Preferred starting compounds for the process of this invention are those of Formula II carrying as the substituent $R_2$, hydrogen, acetyl, propionyl or butyryl. All starting materials of Formula Ii are known (U.S. Pat. Nos. 3,470,160 and 3,525,757 or can be prepared by esterification of the known compounds.

The preferred species for the microbiological oxidation of this invention is *Botryodiplodia malorum*, especially that designated as *Botryodiplodia malorum* (CBS 13,450).

It is surprising that the Δ⁵-steroids of Formula II can be hydroxylated in the 7β-position in this manner since it is known that the corresponding Δ⁴-steroids are hydroxylated in the 7α-position with *Botryodiplodia malorum* (See, e.g., European Patent Application No. 0 014 991).

It has been known for a long time that the selective blockage of the 3-hydroxy group of 3β,7β-dihydroxy-Δ⁵-steroids causes considerable difficulties (J. Amer. Chem. Soc. 74:3310 [1952]). Furthermore, recent experiments have shown that reaction of such compounds with, for example, trimethylacetyl chloride or triphenylchloromethane, agents conventionally employed for the selective blockage of sterically unhindered hydroxy groups in addition to sterically hindered hydroxy groups, does not lead to the desired blocked compounds.

Surprisingly, in accordance with the optional second step of this invention, the selective blockage of the 3β-hydroxy group of the compounds of Formula I is achieved if these compounds are reacted with trimethylacetic anhydride, preferably with the use of 4-dimethylaminopyridine or 4-pyrrolidinopyridine as a catalyst, or if these compounds are reacted with tert-butyldimethylsilyl chloride, with dimethyl-2-(3-methylbutyl)silyl chloride, or tribenzylsilyl chloride, preferably with the use of an organic base, (e.g., pyridine, imidazole, triethylamine, 4-dimethylaminopyridine, lutidine, collidine, etc). Such reactions, for example, can be conducted by analogy to the reactions in the Examples herein. All of these reactions can be conducted under fully conventional conditions determined using fully conventional considerations and described, e.g., in Synthesis 1972, 619–621 and German Pat. No. 19 03 118.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all tempreatures are set forth uncorrected in degrees Celsius; unless otherwise indicated, all parts and percentages are by weight.

The following examples demonstrate the process of this invention and also the commercial exploitability of the process products for the manufacture of the conventional aldosterone-anatagonistically active 6β,7β;15β,16β-dimethylene-3-oxo-17α-pregn-4-ene-21,17-carbolactone.

(A) EXAMPLES RELATING TO THE PREPARATION OF THE COMPOUNDS OF THIS INVENTION

EXAMPLE 1

A 2-liter Erlenmeyer flask containing 500 ml of a nutrient solution, sterilized in an autoclave for 30 minutes at 120° C. and made up of 1% glucose and 1% soybean meal, adjusted to pH 6.2, is inoculated with a slanted-tube culture of the strain *Botryodiplodia malorum* (CBS 13450) and shaken for 2½ days on a rotary shaker.

This germination culture is used to inoculate a 20-liter preliminary fermentor filled with 15 l of a medium having the same composition as the germination culture and having been sterilized for 60 minutes at 121° C. and under 1.1 atm. gauge. With the addition of silicone SH as the defrother, germination is carried out for 24 hours at 29° C. and a pressure of 0.7 atm. gauge under aeration (15 l/min) and agitation (220 rpm).

Thereafter, 0.9 liter of this culture is withdrawn under sterile conditions and used to inoculate a 20-liter main fermentor charged with 14 l of a nutrient medium sterilized as described above and having the same composition as the preliminary fermentation culture. After an incubating period of 12 hours under preliminary fermentor conditions, a pasteurized suspension of 30 g of extremely finely ground 3β-hydroxy-15β,16β-methylene-5-androsten-17-one in 2,250 ml of 1% aqueous "Tween 80" solution is added thereto, and the mixture is further stirred and aerated. The progress of fermentation is controlled by taking samples which are extracted by means of methyl isobutyl ketone and analyzed by thin-layer chromatography. After a contact period of 48 hours, the substrate conversion is complete. The culture broth is freed of fungal mycelium by centrifuging in a continuous centrifuge; the clear filtrate is extracted three times with respectively 10 l of methyl isobutyl ketone, and the extracts are combined with the extract of the mycelium, likewise extrated with methyl isobutyl ketone. After concentrating the solution in a forced circulation evaporator, the mixture is subsequently concentrated to dryness at a bath temperature of 50° C. under vacuum in a rotary evaporator. The oily-crystalline residue is taken up in isopropyl ether and vacuum-filtered through paper filters. After four hours of drying at 70° C. in a vacuum drying chamber, 23.6 g of 3β,7β-dihydroxy-15β,16β-methylene-5-androsten-17-one is obtained, mp 199°–202° C.

EXAMPLE 2

Under the conditions of Example 1, 22.5 g of 3β-acetoxy-15β,16β-methylene-5-androsten-17-one is fermented with *Botryodiplodia malorum*, thus obtaining 16.3 g of 3β,7β-dihydroxy-15β,16β-methylene-5-androsten-17-one, mp 197°–200° C.

EXAMPLE 3

Under the conditions of Example 1, 22.5 g of 3β-hydroxy-15β,16β-methylene-17α-pregn-5-ene-21,17-carbolactone is incubated with *Botryodiplodia malorum*, thus producing 16.8 g of 3β,7β-dihydroxy-15β,16β-methylene-17α-pregn-5-ene-21,17-carbolactone, mp 173°–175° C.

EXAMPLE 4

A solution of 195 g of 3β,7β-dihydroxy-15β,16β-methylene-5-androsten-17-one in 1,460 ml of pyridine is combined with 293 ml of pivalic anhydride and 31 g of dimethylaminopyridine. After a reaction period of 72 hours at room temperature, the crude product is precipitated with 15 l of ice water, vacuum-filtered, washed, and dried at 60° C. Recrystallization from acetone-dichloromethane yields 185.4 g of 7β-hydroxy-15β,16β-methylene-3β-pivaloyloxy-5-androsten-17-one, mp 236° C. $[\alpha]_D = -45°$ (chloroform).

EXAMPLE 5

A solution of 120 g of 3β,7β-dihydroxy-15β,16β-methylene-5-androsten-17-one in 1,000 ml of dimethylformamide is combined with 31 g of imidazole and cooled to −20° C. Within 2 hours, 63 g of tert.-butyldimethylchlorosilane in 450 ml of dimethylformamide is added dropwise to the reaction mixture, and the latter is agitated for another hour. The reaction product is precipitated with sodium-chloride-containing water, filtered off, washed with water, and dissolved in methylene chloride. The solution is dried over sodium sulfate and evaporated. After chromatography on silica gel with hexane-acetone, 128.8 g of 3β-(tert.-butyldimethylsilyloxy)-7β-hydroxy-15β,16β-methylene-5-androsten-17-one is obtained.

EXAMPLE 6

A solution of 100 g of 3β,7β-dihydroxy-15β,16β-methylene-5-androsten-17-one in 2.5 l of tetrahydrofuran and 250 ml of pyridine is cooled to −20° C. and combined within one hour with 88 ml of dimethyl-2-(3- methylbutyl)silyl chloride whereafter the mixture is agitated for 4 hours at this temperature. Then the mixture is combined with 50 ml of methanol and concentrated under vacuum. The crude product is chromatographed on silica gel with methylene chloride-acetone, thus obtaining 98.5 g of 3β-[dimethyl-2-(3-methylbutyl)silyloxy]-7β-hydroxy-15β,16β-methylene-5-androsten-17-one as an oil. $[\alpha]_D = -36°$ (chloroform).

EXAMPLE 7

A solution of 15.7 g of 3β,7β-dihydroxy-15β,16β-methylene-5-androsten-17-one in 750 ml of methylene chloride is combined with 9 ml of triethylamine and 200 mg of dimethylaminopyridine and cooled to $-20°$ C. Within 30 minutes, 19.4 g of tribenzylsilyl chloride in 10 ml of methylene chloride is added dropwise thereto. The reaction mixture is stirred for one hour at $-20°$ C. and one hour at 0° C., diluted with methylene chloride, and washed with 1 N hydrochloric acid, saturated sodium bicarbonate solution, and water. After drying over sodium sulfate, the mixture is concentrated under vacuum. Chromatography on silica gel with hexane-acetone yields 27.5 g of 3β-tribenzylsilyloxy-7β-hydroxy-15β,16β-methylene-5-androsten-17-one.

EXAMPLE 8

16.0 g of 3β,7β-dihydroxy-15β,16β-methylene-17α-pregn-5-ene-21,17-carbolactone is dissolved in 130 ml of dimethylformamide; the solution is combined with 4 g of imidazole and cooled to $-20°$ C. Within 30 minutes, 8 g of tert.-butyldimethylchlorosilane in 60 ml of dimethylformamide is added dropwise thereto, and the mixture is stirred for 2 hours under further cooling. The reaction solution is poured into water, the thus-precipitated product is filtered off, washed, and dried. The crude product is chromatographed with acetone-hexane on silica gel. Yield: 15.4 g of 3β-(tert.-butyldimethylsilyloxy)-7β-hydroxy-15β,16β-methylene-17α-pregn-5-ene-21,17-carbolactone.

(B) EXAMPLES FOR THE COMMERCIAL EXPLOITABILITY OF THE COMPOUNDS ACCORDING TO THE INVENTION

EXAMPLE 1

(a) A suspension of 160 g of 7β-hydroxy-15β,16β-methylene-3β-pivaloyloxy-5-androsten-17-one in 1,600 ml of toluene is combined at 80° C. within 2 hours with 160 ml of 80% strength tert.-butyl hydroperoxide in 475 ml of toluene, after the addition of 1.6 g of vanadium-(IV) oxide acetylacetonate. After cooling, the solution is washed with water, dried over sodium sulfate, and evaporated under vacuum. Yield: 171 g of 5,6β-epoxy-7β-hydroxy-15β,16β-methylene-3β-pivaloyloxy-5β-androstan-17-one. A sample recrystallized from acetone-hexane melts at 220° C. $[\alpha]_D = -12°$ (chloroform).

(b) A solution of 169 g of 5,6β-epoxy-7β-hydroxy-15β,16β-methylene-3β-pivaloyloxy-5β-androstan-17-one in a mixture of respectively 340 ml of dichloromethane, tetrachloromethane, and pyridine is combined with 200 g of triphenylphosphine and stirred for 2 hours at room temperature. The reaction solution is washed with water, dried over sodium sulfate, and evaporated to dryness under vacuum. The residue is stirred up with 310 ml of ethanol and filtered. The filter cake is washed with 175 ml of ethanol and dried under vacuum, thus obtaining 139.2 g of 7α-chloro-5,6β-epoxy-15β,16β-methylene-3β-pivaloyloxy-5β-androstan-17-one. An analytical sample, recrystallized from acetone-hexane, has a melting point of 228° C. $[\alpha]_D = -100°$ (chloroform).

(c) A solution of 196 g of 7α-chloro-5,6β-epoxy-15β,16β-methylene-3β-pivaloyloxy-5β-androstan-17-one in 500 ml of acetic acid and 800 ml of tetrahydrofuran is combined at 70° C. with 392 g of zinc dust in two portions at an interval of 30 minutes, and stirred for one hour at this temperature. After cooling, the zinc is filtered off over "Celite" and washed with 5 l of methylene chloride. The combined filtrates are mixed with 1.5 l of water and neutralized under agitation by the addition of solid sodium bicarbonate. The organic phase is then washed with water, dried over sodium sulfate, and concentrated under vacuum. By trituration of the thus-obtained solid with ethyl acetate, 134.7 g of 5-hydroxy-15β,16β-methylene-3β-pivaloyloxy-5β-androst-6-en-17-one is produced, mp 243° C.

(d) 134 g of 5-hydroxy-15β,16β-methylene-3β-pivaloyloxy-5β-androst-6-en-17-one is dissolved in 1,340 ml of tetrahydrofuran and 670 ml of methanol and combined in succession with 40 g of pulverized potassium hyroxide and 13 g of sodium perchlorate. After 2.5 hours, the mixture is stirred into 8 l of water, neutralized with 20% sulfuric acid, and the thus-precipitated solid is filtered off. After dissolving the solid in methylene chloride and drying same with sodium sulfate, it is concentrated under vacuum. By trituration of the resultant solid with ethyl acetate, 99.8 g of 3β,5-dihydroxy-15β,16β-methylene-5β-androst-6-en-17-one is produced, mp 198° C.

(e) A solution of 26 g of 3β,5-dihydroxy-15β,16β-methtylene-5β-androst-6-en-17-one in 520 ml of ethylene glycol dimethyl ether is agitated with 78 g of zinc-copper and 69 ml of methylene iodide for 4 hours at 80° C. The mixture is then diluted with methylene chloride, washed with saturated ammonium chloride solution and water, dried, and evaporated. The residue is chromatographed on silica gel, thus obtaining 16.3 g of 3β,5-dihydroxy-6β,7β;15β,16β-dimethylene-5β-androstan-17-one, mp 205.5°–207° C.

(f) 25.1 g of 3β,5-dihydroxy-6β,7β;15β,16β-dimethylene-5β-androstan-17-one is dissolved in 500 ml of tetrahydrofuran. Under cooling to 0° C. and under an argon atmosphere, 75.5 g of potassium methylate is added to this solution, and then under agitation 50.4 ml of propargyl alcohol dissolved in 104 ml of tetrahyrofuran is added dropwise thereto. The reaction mixtur is stirred for 20 hours at 0° C. and poured into ice water. After neutralization with dilute sulfuric acid, the thus-precipitated product is filtered off and dried. The crude product is chromatographed on silica gel, thus obtaining 25 g of 17α-(3-hydroxy-1-propinyl)-6β,7β;15β,16β-dimethylene-5β-androstane-3β,5,17β-triol, mp 202°–203° C. (acetone).

(g) 24.5 g of 17α-(3-hydroxy-1-propinyl)-6β,7β;15β,16β-dimethylene-5β-androstane-3β,5,17β-triol is hydrogenated in 250 ml of tetrahydrofuran and 125 ml of methanol in the presence of 3.75 g of palladium on charcoal (10% strength) and 0.5 ml of pyridine until 2 equivalents of hydrogen have been absorbed. The product is filtered off from the catalyst and concentrated by evaporation, thus obtaining 24.7 g of 17α-(3-hydroxypropyl)-6β,7β;15β;16β-dimethylene-5β-androstane-3β,5,17β-triol which is utilized in the subsequent stage without further purification.

(h) A solution of 24.7 g of 17α-(3-hyroxypropyl)-6β,7β;15β,16β-dimethylene-5β-androstane-3β,5,17β- triol in 247 ml of pyridine is combined with a solution of 74.1 g of chromium(VI) oxide in 247 ml of water and 494 ml of pyridine and stirred for 16 hours at 50° C. Thereafter the mixture is diluted with methylene chloride, washed with water, dried, and evaporated. The residue is chromatographed on silica gel. After recrystallization from diisopropyl ether-acetone, the yield is 14.5 g of 6β,7β;15β,16β-dimethylene-3-oxo-17α-pregn-4-ene-21,17-carbolactone, mp 196.5°–197.5° C.

EXAMPLE 2

(a) 128 g of 3β-(tert.-butyldimethylsilyloxy)-7β-hydroxy-15β,16β-methylene-5-androsten-17-one is dissolved in 750 ml of toluene and combined at 80° C. with 500 mg of vanadium(IV) oxide acetylacetonate. To this mixture is added dropwise 460 ml of tert.-butyl hydroperoxide solution (from 100 ml of 80% tert.-butyl hydroperoxide and 400 ml of toluene) and the mixture is left for 1.5 hours at this temperature. After cooling, the mixture is washed with water and saturated sodium chloride solution, dried over sodium sulfate, and evaporated under vacuum. Yield: 126.5 g of 3β-(tert.-butyldimethylsilyloxy)-5,6β-epoxy-7β-hydroxy-15β,16β-methylene-5β-androstan-17-one, mp 189° C. $[\alpha]_D = -8.8°$ (chloroform).

(b) 126 g of 3β-(tert.-butyldimethylsilyloxy)-5,6β-epoxy-7β-hydroxy-15β,16β-methylene-5β-androstan-17-one is dissolved in a mixture of 600 ml of methylene chloride, 600 ml of carbon tetrachloride, and 300 ml of pyridine and stirred with 193.8 g of triphenylphosphine for 2.5 hours. The mixture is then washed with water, dried over sodium sulfate, and concentrated under vacuum. Chromatography on silica gel with hexane-acetone yields 117.4 g of 3β-(tert.-butyldimethylsilyloxy)-7α-chloro-5,6β-epoxy-15β,16β-methylene-5β-androstan-17-one, mp 155.5° C. $[\alpha]_D = -87°$ (chloroform).

(c) 142 g of 3β-(tert.-butyldimethylsilyloxy)-7α-chloro-5,6β-epoxy-15β,16β-methylene-5β-androstan-17-one is dissolved in 400 ml of tetrahydrofuran and 400 ml of methanol and stirred with 1,000 ml of 8% strength sulfuric acid for 1.5 hours at room temperature. The mixture is then diluted with ether, washed with saturated sodium bicarbonate solution and water, dried over sodium sulfate, and concentrated under vacuum. By trituration of the resultant solid with diisopropyl ether, 108 g of 7α-chloro-5,6β-epoxy-3β-hydroxy-15β,16β-methylene-5β-androstan-17-one is obtained, mp 173° C.

(d) 107.5 g of 7α-chloro-5,6β-epoxy-3β-hydroxy-15β,16β-methylene-5β-androstan-17-one is dissolved in 500 ml of acetic acid and 500 ml of tetrahydrofuran and, after the addition of 324 g of zinc dust in three portions, stirred at room temperature for 16 hours. The zinc is then filtered off, the filtrate is diluted with methylene chloride, and washed with sodium bicarbonate solution and water. After drying over sodium sulfate, the product is concentrated under vacuum. By trituration of the thus-obtained solid with ethyl acetate, 91.5 g of 3β,5-dihydroxy-15β,16β-methylene-5β-androst-6-en-17-one is produced, mp 196° C.

EXAMPLE 3

(a) A solution of 133 g of 3β-[dimethyl-2-(3-methylbutyl)silyloxy]-7β-hydroxy-15β,16β-methylene-5-androsten-17-one in 740 ml of toluene is combined at 80° C. with 624 mg of vanadium(IV) oxide acetylacetonate. Within 2 hours, 470 ml of tert.-butyl hydroperoxide solution (from 94 ml of 80% tert.-butyl hydroperoxide and 390 ml of toluene) is added dropwise thereto. The solution is further stirred for one hour at this temperature. After cooling, the solution is washed with water and saturated sodium chloride solution, dried over sodium sulfate, and evaporated under vacuum. Yield: 135 g of 3β-[dimethyl-2-(3-methylbutyl)silyloxy]-5,6β-epoxy-7β-hydroxy-15β,16β-methylene-5β-androstan-17-one as an oil. $[\alpha]_D = -16°$ (chloroform).

(b) 134 g of 3β-[dimethyl-2-(3-methylbutyl)silyloxy]-5,6β-epoxy-7β-hydroxy-15β,16β-methylene-5β-androstan-17-one is dissolved in a mixture of 1,200 ml of methylene chloride, 1,200 ml of carbon tetrachloride, and 600 ml of pyridine. The solution is combined with 140 g of triphenylphosphine and agitated for 3 hours at room temperature. The mixture is then washed with water, dried over sodium sulfate and concentrated under vacuum. Chromatography on silica gel with hexane-acetone yields 126.4 g of 7α-chloro-3β-[dimethyl-2-(3-methylbutyl)silyloxy]-5,6β-epoxy-15β,16β-methylene-5β-androstan-17-one as an oil. $[\alpha]_D = -72°$ (chloroform).

(c) A solution of 107 g of 7α-chloro-3β-[dimethyl-2-(3-methylbutyl)silyloxy]-5,6β-epoxy-15β,16β-methylene-5β-androstan-17-one in a mixture of 500 ml of tetrahydrofuran and 500 ml of methanol is combined with 100 ml of 8% strength sulfuric acid and stirred for 1.5 hours at room temperature. The mixture is then diluted with ether, washed with saturated sodium bicarbonate solution and water, dried over sodium sulfate, and concentrated under vacuum. By triturating the thus-obtained solid with diisopropyl ether, 74.5 g of 7α-chloro-5,6β-epoxy-3β-hydroxy-15β,16β-methylene-5β-androstan-17-one is obtained, mp 173.5° C.

EXAMPLE 4

(a) 24 g of 3β-tribenzylsilyloxy-7β-hydroxy-15β,16β-methylene-5-androsten-17-one is dissolved in 50 ml of toluene, combined with 500 mg of vanadium(IV) oxide acetylacetonate, and heated to 80° C. A solution of 75 ml tert.-butyl hydroperoxide (10 ml 80% tert.-butyl hydroperoxide in 100 ml of toluene) is added dropwise to the reaction mixture, and the latter is allowed to stand for 1.5 hours at this temperature. After cooling, the mixture is washed with water and saturated sodium chloride solution, dried, and evaporated under vacuum, thus obtaining 24.5 g of 3β-tribenzylsilyloxy-5,6β-epoxy-7β-hydroxy-15β,16β-methylene-5β-androstan-17-one.

(b) 24 g of 3β-tribenzylsilyloxy-5,6β-epoxy-7β-hydroxy-15β,16β-methylene-5β-androstan-17-one is dissolved in a mixture of 250 ml of methylene chloride, 250 ml of carbon tetrachloride, and 125 ml of pyridine and stirred with 24 g of triphenylphosphine for 3 hours. The mixture is then washed with water, dried over sodium sulfate, and concentrated under vacuum. After chromatography on silica gel with hexane-acetone, 19.8 g of 3β-tribenzylsilyloxy-7α-chloro-5,6β-epoxy-15β,16β-methylene-5β-androstan-17-one is obtained.

(c) 19 g of 3β-tribenzylsilyloxy-7α-chloro-5,6β-epoxy-15β,16β-methylene-5β-androstan-17-one is dissolved in 50 ml of tetrahydrofuran and 50 ml of methanol and agitated with 15 ml of 8% sulfuric acid for 2 hours at room temperature. The mixture is thereafter diluted with ether, washed with saturated sodium bicarbonate solution and water, dried over sodium sulfate, and concentrated under vacuum. By trituration of the thus-obtained solid with diisopropyl ether, 8.7 g of 7α-chloro-5,6β-epoxy-3β-hydroxy-15β,16β-methylene-5β-androstan-17-one is obtained, mp 172° C.

EXAMPLE 5

(a) 15.0 g of 3β-(tert.-butyldimethylsilyloxy)-7β-hydroxy-15β,16β-methtylene-17α-pregn-5-ene-21,17-carbolactone is converted analogously to the directions in 2(a)-2(d) into 3β,5-dihydroxy-15β,16β-methylene-5β,17α-pregn-6-ene-21,17-carbolactone. Yield: 10.3 g, mp 236° C.

(b) 5 g of 3β,5-dihydroxy-15β,16β-methylene-5β,7α-pregn-6-ene-21,17-carbolactone is dissolved in 100 ml of tetrahydrofuran and combined with 15 g of zinc-copper. Within 7 hours, 13.2 ml of methylene iodide is added dropwise thereto in such a way that the temperature does not rise above 30° C., and the mixture is stirred for another 10 hours at room temperature. To remove the metal, the mixture is filtered over "Celite", the filtrate is diluted with methylene chloride and washed with saturated ammonium chloride solution, dried over magnesium sulfate, and concentrated under vacuum. The residue is chromatographed on silica gel, thus obtaining 4.4 g of 3β,5-dihydroxy-6β,7β;15β,16β-dimethylene-5β,17α-pregnane-21,17-carbolactone as an oil.

(c) 2.8 g of 3β,5-dihydroxy-6β,7β;15β,16β-dimethylene-5β,17α-pregnane-21,17-carbolactone is dissolved in 28 ml of pyridine and combined with a solution of 15 g of chromium(VI) oxide in 28 ml of pyridine and 14 ml of water. The mixture is agitated for 16 hours at 50° C. After cooling, the mixture is diluted with methylene chloride, washed with water, dried over magnesium sulfate, and concentrated under vacuum. The residue is chromatographed on silica gel, thus obtaining 2.3 g of 6β,7β;15β,16β-dimethylene-3-oxo-17α-pregn-4-ene-21,17-carbolactone, mp 198°-198.5° C.

The preceding examples can be repeated with similar success by substituting the generically or specifically described reactants and/or operating conditions of this invention for those used in the preceding examples. From the foregoing description, one skilled in the art can easily ascertain the essential characteristics of this inention, and without departing from the spirit and scope thereof, can make various changes and modifications of the invention to adapt it to various usages and conditions.

What is claimed is:

1. A process for preparing a 3β,7β-hydroxy-Δ⁵-steroid of the formula

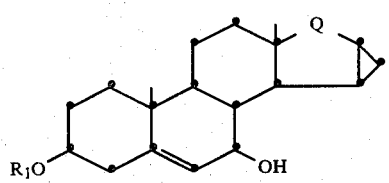

wherein
Q is

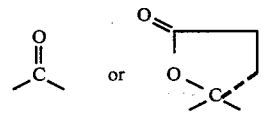

and
$R_1$ is hydrogen,
comprising fermenting a 3β-hydroxy-Δ⁵-steroid of the formula

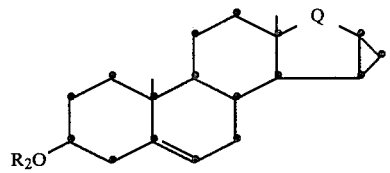

wherein
Q is as defined above, and
$R_2$ is hydrogen or alkanoyl of 2-6 carbon atoms,
with a culture of *Botryodiplodia malorum* to obtain the corresponding 3β,7β-dihydroxy-Δ⁵-steroid; and,
isolating the 3β,7β-dihydroxy-Δ⁵-steroid.

2. A process of claim 1, for preparing a 3β,7β-dihydroxy-Δ⁵-steroid of the formula

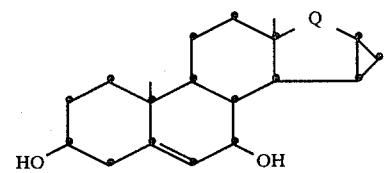

wherein
Q is as defined in claim 1, consisting essentially of fermenting a compound of the formula

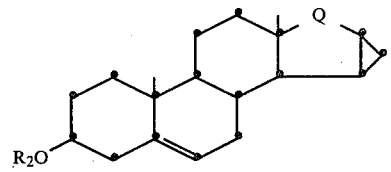

wherein Q and $R_2$ are as defined in claim 1, with a culture of *Botryodiplodia malorum*, and isolating the 3β,7β-dihydroxy-Δ⁵-steroid.

3. A process of claim 1, for preparing a 3β-modified hydroxy steroid wherein $R_1$ is trimethylacetyl, tert-butyldimethylsilyl, dimethyl-2-(3-methylbutyl)silyl or tribenzylsilyl,
comprising conducting the fermenting step,
then reacting the resultant product with trimethylacetic anhydride, tert-butyl-dimethylsilyl chloride, dimethyl-2-(3-methylbutyl)silyl chloride, or tribenzylsilyl chloride, and then
isolating the resultant 7β-hydroxy-Δ⁵-steroid.

4. A process of claim 1, 2 or 3, wherein the fermentation step is conducted with a culture of *Botryodiplodia malorum* (CBS 13 450).

5. A process of claim 1, wherein $R_2$ is H, acetyl, propionyl or butyryl.

* * * * *